Oct. 10, 1944. J. H. BONHARD Plant Pat. 645
CARNATION PLANT
Filed March 11, 1944
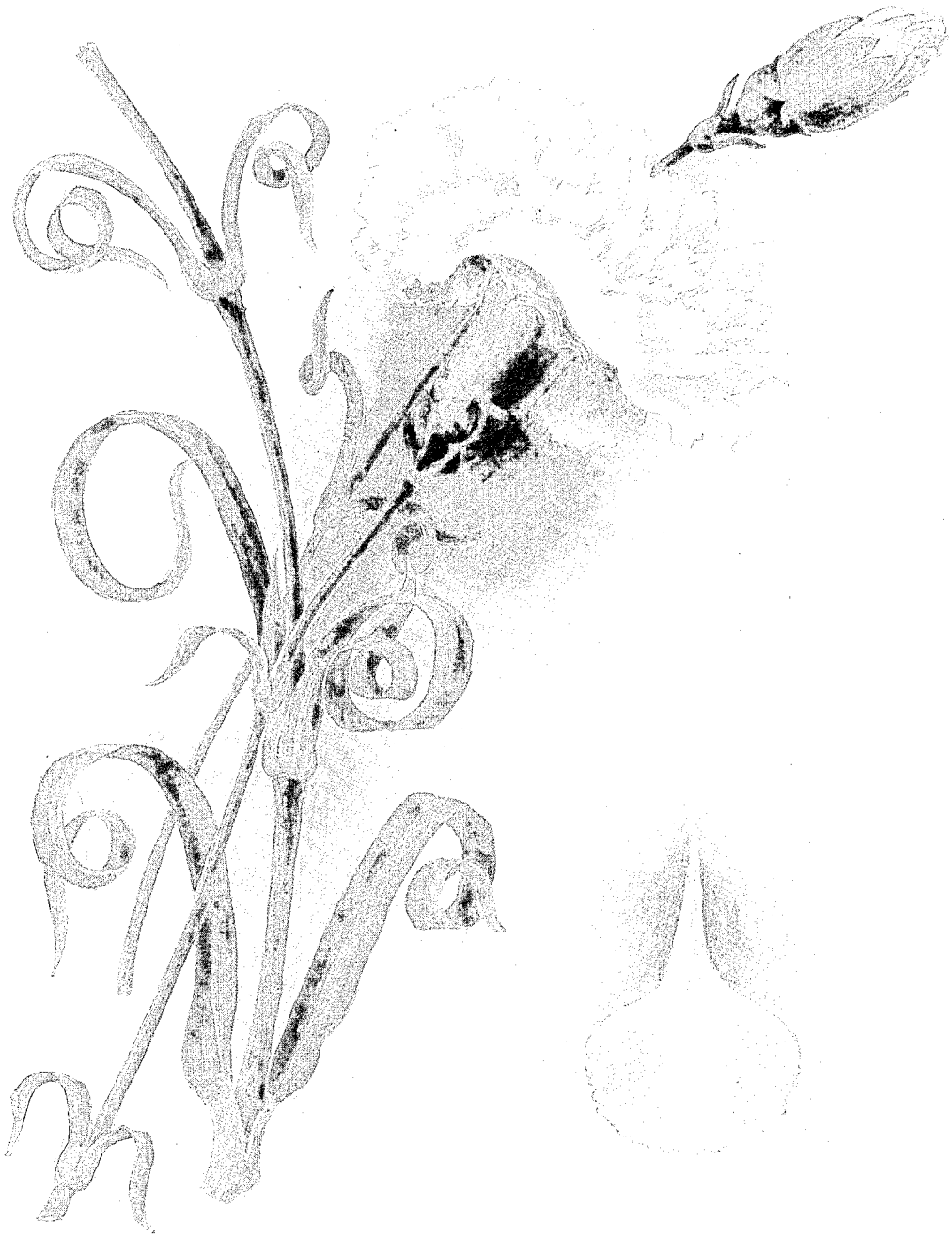
WITNESS
Addison E. Avery
INVENTOR,
John Harry Bonhard, by
Kummler Kummler & Davis,
Attorneys.

Patented Oct. 10, 1944

Plant Pat. 645

UNITED STATES PATENT OFFICE

645

CARNATION PLANT

John Harry Bonhard, West Chicago, Ill., assignor to Geo. J. Ball, Inc., West Chicago, Ill., a corporation of Illinois Application March 11, 1944, Serial No. 526,001

1 Claim. (Cl. 47—60)

The present invention relates to a new and distinct variety of carnation plant which is particularly desirable for commercial purposes. It originated as a sport on a pink carnation plant known as "Charm." This new variety has been reproduced by cuttings, it has been propagated through several generations starting in 1941, and its characteristics appear to be permanently fixed.

Distinctive features of this new variety are its early blooming habit, its rich bright Castilian Red coloring, its unusually large blooms with heavy petalage with good lasting qualities, the immediate opening of its blooms upon cutting; its freedom from the usual carnation diseases, its tough calyxes which seldom split or burst, and the long, sturdy stems of its flowers.

This new variety in plant structure is similar in growth to its parent "Charm," but differs therefrom in the color of the blossom. Its calyx consists of the usual tube (which in this carnation is very large) divided only near the top into five sepals which are reinforced at the base of the tube by four stout lobate sepals which in turn are reinforced by two strong bracts webbed together at their bases. Thus the structure of this calyx with its deep convex puffs at the apex of each lobe is large enough to allow for expansion and growth of the flower without the splitting or parting of its segments.

The accompanying illustration shows in full color a typical bloom with its stem broken into two lengths, one overlying the other to indicate the nature of the stem and leaf structure. The calyx tube is marked by longitudinal fiber lines which do not appear in the illustration where the artist has sought rather to bring out the color values and form shades. The illustration also includes a petal removed from the flower to show its general shape and color distribution, the whitish stem portion of the petal is normally hidden in the calyx tube and the flower is Red from all points of view. The original painting is full size.

The following is a detailed description of my new variety:

Botanic classification: *Dianthus caryophyllus.*

*Flower*

Blooming habit: Prolific and recurrent.
Bloom:
- *Size.*—3¼ to 4 inches in diameter.
- *Borne.*—Singly.
- *Form.*—Symmetrical perimeter with flat top.
- *Stems.*—Extremely long and sturdy, 7/16 inch in diameter at base.
- *Petalage.*—Fully double with long delicate serrated petals, 2½ inches long including the shank and 1¾ inches wide.
- *Color.*—Bright Castilian Red.
- *Discoloration.*—None.
- *Texture.*—Velvety but firm and very little affected by wet or hot weather.
- *Appearance.*—Inside—closely fitted large petals. Outside—symmetrical, full blown, pleasing.
- *Persistence.*—Very persistent.
- *Fragrance.*—Delicate, slightly clovelike.
- *Disease resistance.*—Above average.
- *Lasting quality.*—Extremely long-lasting on plant and better than average as cut flower.

Bud:
- *Size.*—Large.
- *Form.*—Long, cylindrical body.
- *Color.*—Pale Grey-Green.
- *Sepals.*—5 sharply pointed.
- *Calyx.*—Strong and firm.

*Genital organs*

Stamens:
- *Anthers.*—Length—approximately 1 inch. Number—5, mostly abortive. Color—White. Arrangement—evenly distributed around base of ovary.
- *Pollen.*—Scarce. Color—Yellow.

Pistils:
- *Styles.*—Length—one inch. Number—2.
- *Stigma.*—Color—Red with Pinkish bloom or tinge.

Ovaries: One.
Fruit:
- *Fertility.*—Has not been tried.
- *Shape.*—Oval.
- *Color at maturity.*—Light Brown.

*Plant*

Form: Bushy, with many branches.
Height: 4 feet.
Foliage:
- *Color.*—Grey-Green. New foliage—delicate light Grey-Green. Old foliage—dark Grey-Green.
- *Size of leaf.*—5 inches in length by ¼" to ½" wide.
- *Texture.*—Firm.
- *Shape.*—Narrow tapering and curled.

The color designations according to "A Dictionary of Color" by Maerz and Paul are as follows:

| Section | Color | Plate | Letter | Number |
|---|---|---|---|---|
| Main body color flower | Castilian Red | 1 | L | 10 |
| Underside or back of petals. | | 3 | K | 3 |
| Calyx | | 19 | L | 8 |
| Grey-Green on leaf produced by surface bloom. | | 29 | E | 5 |
| Dark body proper leaf color. | | 24 | L | 6 |
| Stem | | 24 | H | 5 |
| Bud: Grey-Green | Olivine | 18 | C | 6 |
| Merging into Yellow-Green. | | 18 | K | 6 |
| Petals of bud | Castilian Red | 1 | L | 10 |

This new variety of carnation plant is easily distinguished from other varieties by its rich and conspicuous coloring, and extremely large blossoms borne on long, stiff but graceful stems. It has few side shoots and no "grassiness." Its Grey-Green leaves are unusually wide near the stem with long blades tapered to a point and convolutely curled. Its stems are firm and sturdy, measuring about $\frac{7}{16}$ of an inch in diameter at their bases and $\frac{3}{32}$ of an inch near the flower. The internodes are about 5 to 5½ inches long with 6 nodes to a stem measuring about 30 inches. It is a remontant carnation plant, with freedom and steadiness in producing blooms.

It grows exactly like its parent "Charm" but the color of the flower closely resembles that of King Cardinal. This new variety opens more freely in winter than does King Cardinal. January and February are months when carnations are in high demand—especially for Valentine's day. The petals of King Cardinal adhere and therefore, the flowers have to be put in water for a couple of days before they open. This new variety does not have this bad habit but opens freely when first cut. It also is not affected by the diseases that King Cardinal is afflicted with.

When the blooms of my new variety are first cut they have a delicate, slightly clovelike fragrance and as the cut flowers age, the spicy perfume becomes more pronounced.

Being long-lasting as a cut flower, with no discoloration until after the 5th day and having desirable fragrance, color, size and resistance to disease, this new variety of carnation is an attractive commercial product.

Thus having disclosed my invention, I claim:

A new and distinct variety of carnation plant with features in combination substantially as shown and described, characterized particularly by the brilliant Castilian Red color, the large size and long-keeping quality of its blooms, its ability to open its blooms promptly when cut, its resistance to diseases peculiar to carnations, its freedom from splitting calyxes, and its long sturdy stems.

JOHN HARRY BONHARD.